(12) United States Patent
Matsuo et al.

(10) Patent No.: US 8,501,998 B2
(45) Date of Patent: Aug. 6, 2013

(54) METHOD FOR PRODUCING POLYOXYALKYLENE DERIVATIVE AND POLYOXYALKYLENE DERIVATIVE

(75) Inventors: Satoshi Matsuo, Kanagawa (JP); Kazuhiro Hashimoto, Kanagawa (JP); Ken-ichiro Nakamoto, Kanagawa (JP); Chika Itoh, Kanagawa (JP)

(73) Assignee: NOF Corporation, Tokyo (JP)

( * ) Notice: Subject to any disclaimer, the term of this patent is extended or adjusted under 35 U.S.C. 154(b) by 577 days.

(21) Appl. No.: 12/751,150

(22) Filed: Mar. 31, 2010

(65) Prior Publication Data

US 2010/0256423 A1    Oct. 7, 2010

(30) Foreign Application Priority Data

Mar. 31, 2009  (JP) .............................. P2009-085188

(51) Int. Cl.
*C07C 41/09* (2006.01)
*C07C 43/11* (2006.01)

(52) U.S. Cl.
CPC ................ *C07C 41/09* (2013.01); *C07C 43/11* (2013.01)
USPC ............ 568/623; 568/620; 568/621; 568/624

(58) Field of Classification Search
CPC ............................... C07C 41/09; C07C 43/11
See application file for complete search history.

(56) References Cited

U.S. PATENT DOCUMENTS

| | | | | | |
|---|---|---|---|---|---|
| 2,948,757 | A | * | 8/1960 | Rogers, Jr. et al. | 568/624 |
| 3,173,790 | A | * | 3/1965 | Dersch et al. | 430/602 |
| 3,278,496 | A | * | 10/1966 | Le Fave et al. | 528/360 |
| 5,415,733 | A | * | 5/1995 | Robinson et al. | 162/5 |
| 2002/0120075 | A1 | | 8/2002 | Yasukohchi et al. | |

FOREIGN PATENT DOCUMENTS

JP    11-335460 A    12/1999

* cited by examiner

*Primary Examiner* — Rosalynd Keys
(74) *Attorney, Agent, or Firm* — Sughrue Mion, PLLC

(57) ABSTRACT

A method for producing a polyoxyalkylene derivative represented by the following general formula (1):

$$Z\text{-}[(OA)_n\text{-}OH]_m \qquad (1)$$

wherein Z is a residue of glycerin or diglycerin, OA is an oxyalkylene group having 2 to 4 carbon atoms, n is an average number of moles of the oxyalkylene group added and is 80 to 800, and m is 3 to 4,
the method comprising steps (A), (B), (C), (D), (E), and (F) defined in the present description.

2 Claims, 1 Drawing Sheet

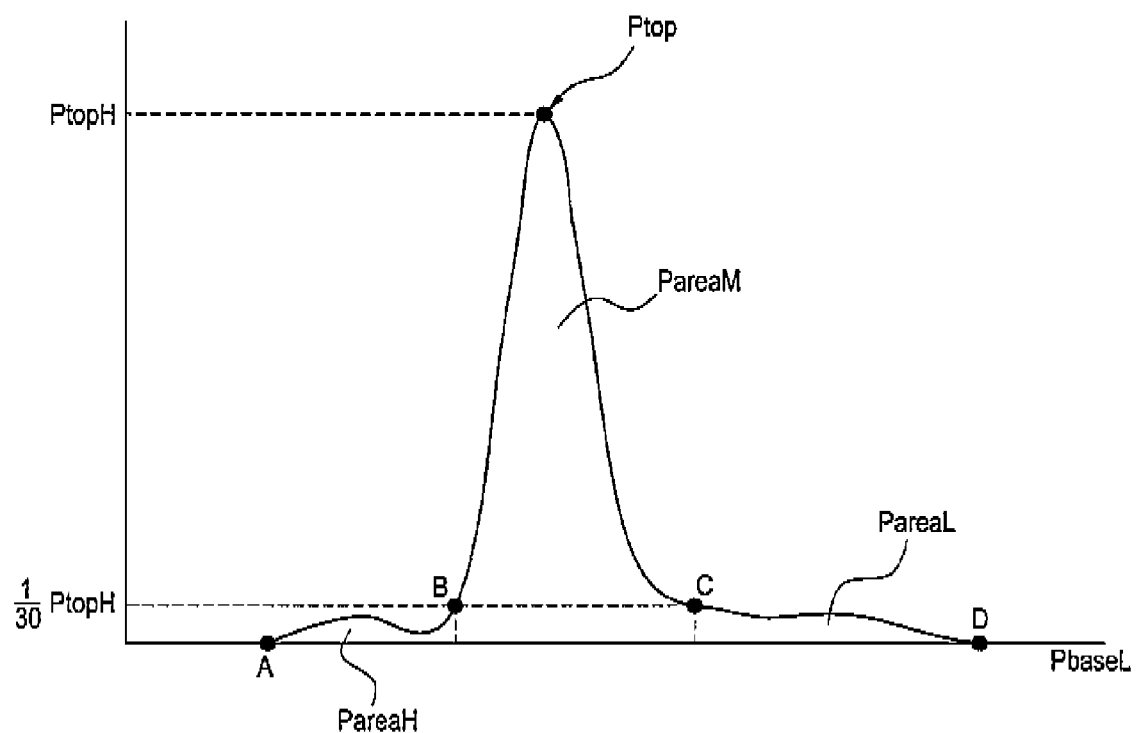

METHOD FOR PRODUCING POLYOXYALKYLENE DERIVATIVE AND POLYOXYALKYLENE DERIVATIVE

FIELD OF THE INVENTION

The present invention relates to a method for producing a polyoxyalkylene derivative. More particularly, it relates to a method for producing a highly pure and high-molecular-weight polyoxyalkylene derivative having a narrow molecular weight distribution and containing only a small amount of impurities.

BACKGROUND OF THE INVENTION

Terminal modified polyoxyalkylene derivatives have recently been engaging attention as an important carrier for drug delivery systems in pharmaceutical fields. As the polyoxyalkylene derivatives which are starting materials to be used on this occasion, there have been known monofunctional compounds having one hydroxyl group, which are obtained by addition polymerization of an alkylene oxide to an aliphatic alcohol or an aromatic alcohol, and multifunctional compounds having two or more hydroxyl groups, which are obtained by addition polymerization of an alkylene oxide to a polyhydric alcohol such as glycerin or diglycerin. Particularly, in the case of the multifunctional derivatives, a large number of a drug can be introduced into one molecule and it becomes possible to increase the concentration in blood. Moreover, since the multifunctional derivatives exhibit gel performance through crosslinking the oxyalkylene chains having hydrophilicity at many points, they have been used in applications as sealant materials such as adhesion inhibitors and wound dressing agents. For these reasons, trifunctional and tetrafunctional polyoxyalkylene derivatives have become currently important materials indispensable in pharmaceutical fields.

JP-A-11-335460 proposes a method for producing an oxirane compound having one hydroxyl group wherein metal sodium, metal potassium, or an alcohol solution of the raw material is used as an alkali catalyst for obtaining a highly pure oxirane derivative. In the production of the trifunctional and tetrafunctional polyoxyalkylene derivatives, there is known a method of using glycerin or diglycerin as a starting material, respectively, and subjecting an alkylene oxide to addition reaction using the alkali catalyst. In general, among the alkali catalysts, the use of metal sodium or metal potassium results in low contamination of water and is suitable for the production of a highly pure oxirane derivative but these alkali catalysts show low solubility in glycerin and diglycerin and hence it is impossible to add a necessary amount of the catalyst for producing a high-molecular-weight compound. In this case, an alkali catalyst such as potassium hydroxide, sodium hydroxide, sodium methoxide, or potassium t-butoxide is employed.

A problem on the production is that, when the alcohol derived from the catalyst and water contained in the raw material remain at the start of the reaction, the alkylene oxide is added thereto to form, as by-products, monofunctional and difunctional impurities having one and two hydroxyl groups, respectively, which have molecular weight lower than that of the objective compound. Usually, in order to suppress the formation of these impurities as by-products, water removal or alcohol removal is carried out but, in the production of the trifunctional or tetrafunctional polyoxyalkylene derivative, since glycerin or diglycerin as the raw material has a high viscosity, it is difficult to remove water or the alcohol by evaporation. In this case, as a means for decreasing the viscosity, it is considered to carry out the water removal and alcohol removal at higher temperature but self-condensation of glycerin or diglycerin as the raw material occurs owing to the alkaline conditions to form polyglycerin as a by-product in some cases. When the alkylene oxide is added to polyglycerin, tetrafunctional and hexafunctional polyoxyalkylene derivatives having molecular weight higher than that of the objective compound are formed as by-products.

Moreover, as the addition reaction of the alkylene oxide proceeds, the viscosity of the reaction liquid generally increases. Therefore, at the time when it is intended to obtain a high-molecular-weight objective compound, there is a case where the reaction system becomes heterogeneous owing to the high viscosity, polydispersity is deteriorated, and stirring becomes impossible in some cases. In order to avoid the situation, the dilution with an aprotic solvent such as a hydrocarbon solvent is effective but there is a case where a difunctional impurity derived from water contained in the aprotic solvent is formed as a by-product, depending on the amount and timing for dilution.

As above, when monofunctional and difunctional low-molecular-weight impurities and tetrafunctional and hexafunctional high-molecular-weight impurities having molecular weight different from the objective molecular weight, which are formed as by-products in the production, are present in a large amount, a heterogeneous polyoxyalkylene derivative is formed. In the case where the heterogeneous polyoxyalkylene derivative is used, in the drug delivery system field, there is a concern that design evaluation of drug carriers becomes difficult and expected performance of pharmaceuticals cannot be exhibited. On the other hand, in the field of the sealant materials such as adhesion inhibitors and wound dressing agents, since the prediction of gel crosslinking points becomes difficult, there is a concern that objective gel performance cannot be exhibited. There have not yet been obtained a highly pure and high-molecular-weight polyoxyalkylene derivative not containing high-molecular-weight impurities and low-molecular-weight impurities and a producing method thereof, which address solution of these problems.

SUMMARY OF THE INVENTION

An object of the invention is to provide a highly pure and high-molecular-weight polyoxyalkylene derivative useful as a starting material of a terminal modified polyoxyalkylene derivative to be used in the pharmaceutical fields mainly including chemical modification of drugs and the like.

As a result of the extensive studies for solving the above problems, the present inventors have paid attention to the fact that, in the production of the polyoxyalkylene derivative, the physical property of viscosity of glycerin or diglycerin changes with the number of moles of the alkylene oxide added. In general, it is known that glycerin or diglycerin itself has a high viscosity but, when several moles of the alkylene oxide is added thereto, the viscosity once reaches a lower limit and then the viscosity increases as the molecular weight increases to a high molecular weight. Utilizing the characteristic property, by carrying out the water removal and alcohol removal from the alkali catalyst to be added in a state where the viscosity of glycerin or diglycerin is once decreased, the inventors have succeeded in the production of the polyoxyalkylene derivative not containing high-molecular-weight impurities and low-molecular-weight impurities.

At the time when several moles of the alkylene oxide is added, owing to the high viscosity of glycerin or diglycerin, it is necessary to use an alkali catalyst which does not require the water removal and alcohol removal, e.g., metal sodium or metal potassium. These alkali metals have low solubility in glycerin or diglycerin but it is possible to add several moles of the alkylene oxide with a small amount of the catalyst. Namely, the inventors have now found that a highly pure and high-molecular-weight polyoxyalkylene derivative not containing high-molecular-weight impurities and low-molecular-weight impurities can be produced by adding several moles of the alkylene oxide with the alkali catalyst which does not require the water removal and alcohol removal to once decrease the viscosity of the reaction system before the alkylene oxide is added to glycerin or diglycerin until an objective molecular weight is reached and subsequently newly adding an alkali catalyst to effect addition of the alkylene oxide through reaction with water removal and alcohol removal until the objective molecular weight is reached, and thus they have accomplished the invention. The invention is as follows.

(1) A method for producing a polyoxyalkylene derivative represented by the following general formula (1):

(1)

wherein Z is a residue of glycerin or diglycerin, OA is an oxyalkylene group having 2 to 4 carbon atoms, n is an average number of moles of the oxyalkylene group added and is 80 to 800, and m is 3 to 4, the method comprising:

step (A): a step of removing water from glycerin or diglycerin at 90° C. to 170° C. under 3 kPa or lower;

step (B): a step of adding metal sodium or metal potassium as an alkali catalyst in an amount of 0.015 to 1.6% by weight based on the amount of glycerin or diglycerin charged in the step (A) and dissolving the metal at 20 to 110° C.;

step (C): a step of subjecting an alkylene oxide to addition reaction at 50° C. to 110° C. until the average number n of moles of the oxyalkylene group OA added reaches 1 to 10;

step (D): a step of adding an alkali catalyst represented by the following general formula (2) in an amount of 2 to 50% by weight based on glycerin or diglycerin charged in the step (A):

R—OW (2)

wherein R is a hydrocarbon group having 1 to 4 hydrocarbons and W represents either sodium or potassium;

step (E): a step of carrying out alcohol removal at 90 to 130° C. under 15 kPa or lower; and step (F): a step of subjecting an alkylene oxide to addition reaction at 100° C. to 130° C. until the average number n of moles of the oxyalkylene group OA added reaches 80 to 800.

(2) The method for producing a polyoxyalkylene derivative according to the above (1), wherein the above step (F) is a step of subjecting an alkylene oxide to addition reaction at 100° C. to 130° C. until the average number n of moles of the oxyalkylene group OA added reaches 80 to 300, subsequently adding a hydrocarbon solvent in an amount of 30 to 70% by weight based on total weight in the reaction vessel, then removing 20 to 60% by weight of the hydrocarbon solvent in the reaction vessel by evaporation, and subsequently subjecting an alkylene oxide to addition reaction at 100° C. to 130° C. until the average number n of moles of the oxyalkylene group OA added reaches 300 to 800.

(3) A polyoxyalkylene derivative represented by the following general formula (1):

(1)

wherein Z is a residue of glycerin or diglycerin, OA is an oxyalkylene group having 2 to 4 carbon atoms, n is an average number of moles of the oxyalkylene group added and is 80 to 800, and m is 3 to 4, in the polyoxyalkylene derivative, Parea, PareaH, and PareaL satisfying relation:

(PareaH+PareaL)/Parea≦0.05 wherein, when a straight line drawn from an elution-starting point to an elution-ending point on a chromatogram of gel permeation chromatography is designated by PbaseL, total peak area of an upper part from PbaseL is designated by Parea, and height of a peak top Ptop of a maximum peak of refractive index from PbaseL is designated by PtopH, peak area between a point B at which height of an elution curve directing from Ptop to an elution-starting point A from PbaseL is 1/30 of PtopH and the elution-starting point A is designated by PareaH, and peak area between a point C at which height of an elution curve directing from Ptop to an elution-ending point D from PbaseL is 1/30 of PtopH and the elution-ending point D is designated by PareaL.

Since the polyoxyalkylene derivative of the general formula (1) obtained by the producing method of the invention contains only a small amount of high-molecular-weight impurities and low-molecular-weight impurities and is highly pure and has high molecular weight, design evaluation of drug carriers can be strictly conducted and expected performance of pharmaceuticals can be exhibited in the drug delivery system field. In the field of sealant materials such as adhesion inhibitors and wound dressing agents, the number of gel crosslinking points can be precisely predicted and objective gel performance can be exhibited.

Accordingly, when the polyoxyalkylene derivative obtained by the producing method of the invention is used, it becomes possible to provide a terminal modified polyoxyalkylene derivative useful as pharmaceutical uses mainly including drug carriers and sealant materials.

BRIEF DESCRIPTION OF THE DRAWINGS

FIG. 1 is a model drawing of a chromatogram obtained by gel permeation chromatography of a polyoxyalkylene derivative represented by the general formula (1).

DETAILED DESCRIPTION OF THE INVENTION

The following will describe the method for producing the polyoxyalkylene derivative of the invention.

The method for producing the polyoxyalkylene derivative of the invention is a method for producing a polyoxyalkylene derivative represented by the following general formula (1), comprising steps (A), (B), (C), (D), (E), and (F).

(1)

In the above general formula (1), Z is a residue of glycerin or diglycerin. Moreover, in the formula, m is 3 in glycerin and m is 4 in diglycerin.

In the formula, OA is an oxyalkylene group having 2 to 4 carbon atoms. The oxyalkylene group specifically includes an oxyethylene group, an oxypropylene group, an oxybutylene group, an oxytrimethylene group, an oxytetramethylene group, an oxy-1-ethylethylene group, an oxy-1,2-dimethylethylene group, and the like. In general, since smaller number of carbon atoms of the alkylene group shows a higher hydrophilicity, an oxyethylene group is preferred in view of solubility in water.

n is an average number of moles of the oxyalkylene group added and n is an integer of 80 to 800. In general, since one

(1)

having a larger molecular weight shows longer circulation in blood, n is preferably 100 to 800, more preferably 120 to 800, particularly preferably 200 to 800.

The following will describe respective steps (A), (B), (C), (D), (E), and (F) in the producing method of the invention in detail.

The step (A) is a step of subjecting glycerin or diglycerin to azeotropic removal of water. The conditions for removal by evaporation for glycerin removal or diglycerin removal are 90 to 170° C. under a vacuum of 3 kPa or lower, preferably 130 to 170° C. under a vacuum of 3 kPa or lower. In the case of lower than 90° C., the azeotropic removal of water is difficult and there is a concern that a low-molecular-weight impurity derived from water is form as a by-product. Moreover, in the case of higher than 170° C., it is known that dehydrative condensation of glycerin occurs, so that the case is not preferred.

The step (B) is a step of dissolving an alkali catalyst such as metal sodium or metal potassium in glycerin or diglycerin adjusted in the step (A). The amount of the alkali catalyst to be added is 0.015 to 1.6% by weight, preferably 0.03 to 0.8% by weight based on the amount of glycerin or diglycerin to be charged in the step (A). In the case where the amount is larger than 1.6% by weight, the catalyst is not completely dissolved. On the other hand, in the case where the amount is lower than 0.015% by weight, the reaction rate of the addition polymerization is extremely decreased and there is a concern that polydispersity increases owing to an increase in heat hysteresis. In the case where the dissolution temperature is lower than 20° C., solubility decreases and the alkali catalyst remains undissolved and there is a possibility that an alkylene oxide cannot be added owing to a shortage of the catalyst. In the case where the dissolution temperature is higher than 110° C., polyglycerin derived from self-condensation of glycerin or diglycerin as a starting material is formed as a by-product owing to the alkaline conditions and high-molecular-weight impurities resulting from the addition of the alkylene oxide to polyglycerin are formed as by-products.

The step (C) is a step of subjecting an alkylene oxide to addition reaction until the average number n of moles of the oxyalkylene group OA added reaches 1 to 10 moles. The reaction temperature is 50° C. to 110° C., preferably 70 to 110° C. In the case where the reaction temperature is lower than 50° C., the reaction rate becomes very low and there is a concern of an increase in polydispersity and the like owing to an increase in heat hysteresis. Moreover, when the reaction temperature exceeds 110° C. and a high temperature state is invited under alkaline conditions, there is a possibility of the formation of polyglycerin as a by-product. Therefore, the reaction temperature for the addition polymerization of the alkylene oxide is desirably 50 to 110° C.

In the average number of moles of the oxyalkylene group added, n is preferably 1 to 10. With regard to glycerin or diglycerin, the physical property of viscosity changes with the number of moles of the alkylene oxide added. Specifically, it is known that glycerin or diglycerin itself has a high viscosity but, when several moles of the alkylene oxide is added, the viscosity once reaches a lower limit and then the viscosity increases as the molecular weight increases to a high molecular weight. Since the polyoxyalkylene derivative having a decreased viscosity where n is 1 or more is advantageous in alcohol removal in the step (E), further preferred range of n is 3 to 8. In the case where n exceeds 10, efficiency of alcohol removal decreases owing to an increase in viscosity, so that the case is not preferred. As the alkylene oxide for the addition to glycerin or diglycerin, ethylene oxide is preferred.

The step (D) is a step of adding an alkali catalyst to the reaction system. In the step (D), an alkali catalyst represented by the following general formula (2) is added.

$$R-OW \qquad (2)$$

In the above general formula (2), R represents a hydrocarbon group having 1 to 4 and includes a methyl group, an ethyl group, a propyl group, an isopropyl group, a butyl group, a t-butyl group, and the like. Moreover, W represents an alkali metal and includes sodium, potassium, and the like. In general, a lower alcohol has a low boiling point and is prone to the removal of the alcohol. Therefore, in order to suppress the formation of a monofunctional impurity derived from the alcohol, a lower alcohol showing a good efficiency of alcohol removal is advantageous. For this reason, as the alkali catalyst to be used, sodium methoxide where R is a methyl and W is sodium is preferred. As a use form, it is added as either a powder or a liquid of a product diluted with an alcohol.

The amount of the alkali catalyst to be added is 2 to 50% by weight, preferably 20 to 50% by weight based on the amount of charged glycerin or diglycerin adjusted in the step (A). In the case where the amount of the alkali catalyst to be added is less than 2% by weight, the reaction rate of the addition polymerization is extremely decreased and there is a concern of an increase in polydispersity owing to an increase in heat hysteresis. On the other hand, in the case where the amount is more than 50% by weight, vinyl etherification of a polyoxyalkylene terminal end occurs, which is commonly known as a termination reaction in the addition of an alkylene oxide. Thus, there is a concern that deterioration of the polydispersity is invited. Therefore, it is said that the amount of the alkali catalyst is desirably 2 to 50% by weight.

The step (E) is a step of preparing an alcoholate of glycerin or diglycerin, which initiates the addition polymerization. These alcoholates are prepared by exchange reaction where the alkali metal W contained in the alkali catalyst of the above general formula (2) is replaced by the hydrogen atom of the hydroxyl group terminal end of glycerin or diglycerin and the exchange reaction is accelerated by alcohol removal from the reaction system. The conditions for the alcohol removal are 90 to 130° C. under a vacuum of 15 kPa or lower, preferably 100 to 120° C. under a vacuum of 15 kPa or lower. In the case where the alcohol removal temperature is lower than 90° C., the viscosity of the polyoxyalkylene derivative prepared in the step (C) increases. Therefore, the alcohol removal becomes difficult and the alcohol contained in the alkali catalyst of the above general formula (2) remains, so that the formation of the monofunctional impurity derived from the alcohol is unavoidable in the addition polymerization reaction. In the case where the alcohol removal temperature is higher than 130° C., the terminal vinyl etherification occurs owing to the high temperature and there is a concern that the deterioration of the polydispersity is invited. Therefore, the conditions for the alcohol removal are desirably 90 to 130° C. under a vacuum of 15 kPa or lower.

The step (F) is a step of subjecting an alkylene oxide to addition reaction until the average number n of moles of the oxyalkylene group added reaches 80 to 800. The average number n of moles of the oxyalkylene group added is 80 to 800, preferably 100 to 800, more preferably 120 to 800, particularly preferably 200 to 800. In the case where the reaction temperature is lower than 100° C., the addition reaction rate extremely decreases, so that there is a concern that the polydispersity is deteriorated owing to an increase in heat hysteresis or there is a case where the inside of the reaction system becomes a high viscosity owing to the low temperature and thus stirring becomes difficult. In the case where the reaction temperature is higher than 130° C., there is a concern that the terminal vinyl etherification occurs owing to the high temperature and thus the deterioration of the polydispersity is invited.

In the step (F), as the addition polymerization reaction of the alkylene oxide proceeds, the molecular weight of the objective compound increases, so that the viscosity of the reaction liquid generally increases. Therefore, when it is intended to obtain the objective compound having a high molecular weight in the above step (F), the reaction system becomes heterogeneous owing to the high viscosity, the polydispersity is deteriorated, and the stirring becomes impossible in some cases. For decreasing the viscosity, it is effective to take a means of diluting the inside of the reaction system with a hydrocarbon solvent such as toluene. With regard to the average number of moles of the oxyalkylene group when dilution is conducted, n is 80 to 300, preferably 100 to 270, more preferably 120 to 240 in the case of glycerin and n is 80 to 300, preferably 90 to 250, more preferably 100 to 200 in the case of diglycerin.

The hydrocarbon solvent for use in the dilution is not particularly limited as far as it is a solvent which forms an azeotrope with water and, for example, includes toluene, xylene, benzene, ethylbenzene, cyclohexane, methylcyclohexane, and the like, and preferred is toluene. The amount of the solvent to be added is 30 to 70% by weight, preferably 30 to 65% by weight, further preferably 30 to 50% by weight based on the total weight (charged total weight) in the reaction vessel. After the addition, 20 to 60% by weight, preferably 20 to 50% by weight, further preferably 20 to 40% by weight of the amount of the diluting hydrocarbon solvent was removed by evaporation with azeotropic removal of water at 90 to 120° C. In the case where the amount of the hydrocarbon solvent to be added is less than 30% by weight of the charged total weight, there is a case where the viscosity cannot be decreased, the reaction system becomes heterogeneous, the polydispersity is deteriorated, and the stirring becomes impossible in some cases. Moreover, in the case where the amount is more than 70% by weight, the amount of water, which is contained in the hydrocarbon solvent and to be mixed in, increases and there is a concern that water remains after the removal of the hydrocarbon solvent by evaporation. On the other hand, in the case where the amount of the hydrocarbon solvent to be removed by evaporation is less than 20% by weight based on the amount of the diluting hydrocarbon solvent, there is a concern that the azeotropic removal of water is not sufficiently carried out and hence water remains. In the case where the amount is larger than 60% by weight, there is a case where the viscosity cannot be decreased, the reaction system becomes heterogeneous, the polydispersity is deteriorated, and the stirring becomes impossible in some cases.

After the removal of the diluting hydrocarbon solvent by evaporation, the alkylene oxide is subjected to the addition polymerization at 100 to 130° C. until the average number n of moles of the oxyalkylene group added reaches 300 to 800. In the case where the reaction temperature is lower than 100° C., since the addition reaction rate is extremely decreased, there is a concern that the polydispersity is deteriorated owing to an increase in heat hysteresis and there is a case where the inside of the reaction system becomes a high viscosity owing to the low temperature and hence the stirring becomes difficult. In the case where the reaction temperature is higher than 130° C., there is a concern that the terminal vinyl etherification occurs owing to the high temperature and the deterioration of the polydispersity is invited.

The impurities formed as by-products in the production include high-molecular-weight impurities and low-molecular-weight impurities. The high-molecular-weight impurities include compounds obtained by self-condensation of the starting material and addition of the alkylene oxide, which are formed in the steps (A) and (C). A tetrafunctional impurity is formed as a by-product in the case where the starting material is trifunctional glycerin and a hexafunctional impurity is formed as a by-product in the case where the starting material is tetrafunctional diglycerin. In particular, the self-condensation of the starting material is prone to occur under alkaline conditions in the step (C) and high-molecular-weight impurities are formed as by-products.

On the other hand, the low-molecular-weight impurities are a difunctional impurity derived from water and a monofunctional impurity derived from the alcohol. The difunctional impurity is formed as a by-product by the addition of the alkylene oxide to water when water remains in the azeotropic removal of water after the dilution with toluene in the step (A) or (F). The monofunctional impurity is formed as a by-product by the addition of the alkylene oxide to the alcohol when the alcohol derived from the catalyst remains in the step (E).

In the polyoxyalkylene derivative having the structure of the above general formula (1) obtained by the producing method of the invention, Parea, PareaH, and PareaL satisfy relation:

$$(PareaH + PareaL)/Parea \leq 0.05$$

wherein, when a straight line drawn from an elution-starting point to an elution-ending point on a chromatogram of gel permeation chromatography is designated by PbaseL, total peak area of an upper part from PbaseL is designated by Parea, and height of a peak top Ptop of a maximum peak of refractive index from PbaseL is designated by PtopH, peak area between a point B at which height of an elution curve directing from Ptop to the elution-starting point A from PbaseL is 1/30 of PtopH and the elution-starting point A is designated by PareaH, and peak area between a point C at which height of an elution curve directing from Ptop to the elution-ending point D from PbaseL is 1/30 of PtopH and the elution-ending point D is designated by PareaL. However, in the calculation formula, the calculation is performed on only peaks derived from the polyoxyalkylene derivatives excluding peaks originated from the developing solvent used in the gel permeation chromatography and pseudo peaks resulting from base line fluctuation originated from the columns and apparatus used.

In the gel permeation chromatography, SHODEX GPC SYSTEM-11 as a GPC system, SHODEX RI-71 as a differential refractometer, and SHODEX KF804L ($\phi$8 mm×300 mm) as GPC columns are employed. The measurement of samples is performed by connecting three GPC columns in series, controlling the column constant bath temperature at 40° C., letting tetrahydrofuran flow as a developing solvent at a flow rate of 1 ml/minute, and injecting 0.1 ml of a 0.1% by weight solution of a sample. Various measured data are obtained by analyzing an elution curve by the BORWIN GPC calculation program.

FIG. 1 shows a model drawing of a chromatogram obtained by the gel permeation chromatography. PareaH corresponding to the peak range from the point A to the point B shows a tetrafunctional impurity as a high-molecular-weight impurity and corresponds to a peak having a molecular weight 1.3 times or more the objective molecular weight in the case of the trifunctional glycerin raw material, and shows a hexafunctional impurity as a high-molecular-weight impurity and corresponds to a peak having a molecular weight 1.5 times or more the objective molecular weight in the case of the tetrafunctional diglycerin raw material.

PareaL corresponding to the peak range from the point C to the point D shows mono- and difunctional impurities as low-molecular-weight impurities and corresponds to peaks having molecular weight ⅔ time and ⅓ time the objective molecular weight in the case of the trifunctional glycerin raw material, and corresponds to peaks having molecular weight ½ time and ¼ time the objective molecular weight in the case of the tetrafunctional diglycerin raw material.

In the chromatogram obtained in the invention, the purity of the polyoxyalkylene derivative having the structure of the general formula (1) is defined as a total value of (PareaH+ PareaL).

In the polyoxyalkylene derivative of the invention, (PareaH+PareaL)/Parea satisfies 0.05 or less. When (PareaH+ PareaL)/Parea is larger than 0.05, the high-molecular-weight impurities and the low-molecular-weight impurities increases and the purity as a raw material for pharmaceutical uses becomes insufficient, so that there is a concern that precise design evaluation becomes difficult or there is a concern that the performance of products is impaired and thus the case is problematic.

When the amount of the high-molecular-weight impurities and the low-molecular-weight impurities shown in the above is large, there are problems in the drug delivery system field that the design evaluation of drug carriers becomes difficult and expected performance of pharmaceuticals cannot be exhibited. On the other hand, there is a problem in the filed of sealant materials such as adhesion inhibitors and wound dressing agents that the estimation of gel crosslinking points becomes difficult and hence an objective gel performance cannot be exhibited.

These problems can be solved by the producing method of the invention. Namely, since the polyoxyalkylene derivative of the general formula (1) obtained by the producing method of the invention contains only a small amount of the high-molecular-weight impurities and the low-molecular-weight impurities, is highly pure and has a high molecular weight, unlike those obtained by conventional methods. Therefore, the polyoxyalkylene derivative is useful as a starting material of a terminal polyoxyalkylene derivative for use in pharmaceutical uses mainly including drug carriers or sealant materials.

EXAMPLES

The following will explain the present invention in detail with reference to Examples and Comparative Examples. In this regard, the following compound (g) was obtained in Example 1, Comparative Example 1, Comparative Example 2, and Comparative Example 3. The following compound (d) was obtained in Example 2 and Comparative Example 4.

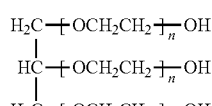

(g)

n = 300

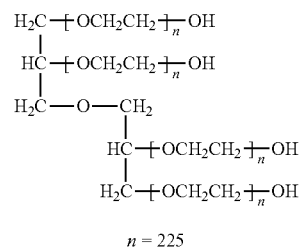

n = 225

Moreover, compounds obtained in Examples and Comparative Examples were analyzed by gel permeation chromatography. The analysis was carried out in accordance with the following method.

<Analytical Method of Gel Permeation Chromatography>

When a straight line drawn from an elution-starting point to an elution-ending point on a chromatogram of gel permeation chromatography is designated by PbaseL, total peak area of an upper part from PbaseL is designated by Parea, and height of the peak top Ptop of a refractive index maximum peak from PbaseL is designated by PtopH, peak area between a point B at which height of an elution curve directing from an elution-starting point A to Ptop from PbaseL is 1/30 of PtopH and a point C at which height of an elution curve directing from Ptop to an elution-ending point D from PbaseL is 1/30 of PtopH is designated by PareaM, peak area between the elution-starting point A and the point B is designated by PareaH, and peak area between the point C and the elution-ending point D is designated by PareaL.

Example 1

Into a four-neck flask fitted with a reflux apparatus, a nitrogen gas-introducing tube, a thermometer, and a mixing apparatus was charged 107 g (about 1.2 mol) of glycerin, and glycerin removal and water removal were conducted at 160° C. under a vacuum condition of 1.07 kPa or lower until the amount of removed substances by evaporation reached 7 g. Then, 0.057 g (0.053% by weight based on the raw material) of metal sodium was added at 50° C. and dissolved at 70° C. The whole amount in the four-neck flask was transferred to a reactor for alkylene oxide addition and ethylene oxide was added at 100° C. until n reached 3.5. After cooling to 40° C., 46 g (43% by weight based on the raw material) of sodium methylate was added and methanol removal was carried out at 120° C. under a vacuum condition of 13.3 kPa or lower for 1 hour. Subsequently, after ethylene oxide was added at 120° C. until n reached 225, 12 kg (38% by weight) of anhydrous toluene was added based on the total weight of the charged substances in the reactor, followed by 30 minutes of stirring at 80° C. At 110° C. under a normal pressure, 4 kg (30% by weight based on the toluene charged into the reactor) was removed by evaporation. Subsequently, ethylene oxide was added at 120° C. until n reached 300 to obtain a compound (g) which is a polyethylene oxide derivative.

As a result of analysis by gel permeation chromatography, the retention times of the elution-starting point A and the elution-ending point D were 18.775 minutes and 24.325 minutes, respectively. The retention time of Ptop was 20.283 and the retention times of the points B and C at which the height of the elution curve from PbaseL reached 1/30 of the height of PtopH were 19.958 minutes and 21.033 minutes, respectively. Parea was 792,238 and PareaM, PareaH, and PareaL were 758,877, 4,761, and 28,600, respectively.

From the results, the following are calculated.

$PareaM/Pareax100=95.8(\%)$ $PareaH/Pareax100=0.6(\%)$ $PareaL/Pareax100=3.6(\%)$ Example 2

Into a four-neck flask fitted with a reflux apparatus, a nitrogen gas-introducing tube, a thermometer, and a mixing apparatus was charged 149 g (about 0.9 mol) of diglycerin, and glycerin removal and water removal were conducted at 170° C. under a vacuum condition of 0.3 kPa or lower until the amount of removed substances by evaporation reached 2 g. Then, 0.114 g (0.077% by weight based on the raw material) of metal sodium was added at 50° C. and dissolved at 70° C. The whole amount in the four-neck flask was transferred to a reactor for alkylene oxide addition and ethylene oxide was added at 100° C. until n reached 5.0. After cooling to 50° C., 45 g (30% by weight based on the raw material) of sodium methylate was added and methanol removal was carried out at 120° C. under a vacuum condition of 13.3 kPa or lower for 1 hour. Subsequently, after ethylene oxide was added at 120° C. until n reached 170, 17 kg (63% by weight) of anhydrous toluene was added based on the total weight of the charged substances in the rector, followed by 1 hours of stirring at 80° C. At 110° C. under a normal pressure, 8 kg (47% by weight based on the toluene charged into the reactor) of toluene was removed by evaporation. Subsequently, ethylene oxide was added at 120° C. until n reached 225 to obtain a compound (d) which is a polyethylene oxide derivative.

As a result of analysis by gel permeation chromatography, the retention times of the elution-starting point A and the elution-ending point D were 19.658 minutes and 24.050 minutes, respectively. The retention time of Ptop was 20.650 and the retention times of the points B and C at which the height of the elution curve from PbaseL reached 1/30 of the height of PtopH were 20.208 minutes and 21.392 minutes, respectively. Parea was 742,644 and PareaM, PareaH, and PareaL were 719,622, 2,971, and 20,0510, respectively.

From the results, the following are calculated.

$PareaM/Pareax100=96.9(\%)$ $PareaH/Pareax100=0.4(\%)$ $PareaL/Pareax100=2.7(\%)$ Comparative Example 1

Into a reactor for alkylene oxide addition were charged 107 g (about 1.2 mol) of glycerin and 46 g (43% by weight based on the raw material) of sodium methylate, and methanol removal was carried out at 80° C. under a vacuum condition of 13.3 kPa or lower for 1 hour. Subsequently, after ethylene oxide was added at 120° C. until n reached 225, 12 kg (38% by weight) of anhydrous toluene was added based on the total weight of the charged substances in the reactor, followed by 30 minutes of stirring at 80° C. At 110° C. under a normal pressure, 4 kg (30% by weight based on the toluene charged into the reactor) of toluene was removed by evaporation. Subsequently, ethylene oxide was added at 120° C. until n reached 300 to obtain a compound (g) which is a polyethylene oxide derivative.

As a result of analysis by gel permeation chromatography, the retention times of the elution-starting point A and the elution-ending point D were 18.800 minutes and 24.442 minutes, respectively. The retention time of Ptop was 20.217 and the retention times of the points B and C at which the height of the elution curve from PbaseL reached 1/30 of the height of PtopH were 19.800 minutes and 21.050 minutes, respectively. Parea was 735,301 and PareaM, PareaH, and PareaL were 670,594, 6,618, and 58,089, respectively.

From the results, the following are calculated.

$PareaM/Pareax100=91.2(\%)$ $PareaH/Pareax100=0.9(\%)$ $PareaL/Pareax100=7.9(\%)$ When comparison with Example 1 was conducted based on the results shown in Table 1, impurities increased such that high-molecular-weight one was 0.9% and low-molecular-weight one was 7.9%, respectively. The reason for the increase of the high-molecular-weight one is that polyglycerin is formed as a by-product at 80° C. under alkaline conditions and the reason for the increase of the low-molecular-weight one is that the methanol removal is insufficient at 80° C. under a vacuum condition of 13.3 kPa or lower.

From the results, it is found difficult to produce a highly pure and high-molecular-weight polyoxyalkylene derivative without the step of decreasing the viscosity by addition polymerization of an alkylene oxide (corresponding to the step (C)).

Comparative Example 2

The amounts of toluene to be added and to be removed by evaporation were changed in the operation procedure of Comparative Example 1 as follows. After ethylene oxide was added until n reached 225, 38 kg (120% by weight) of anhydrous toluene was added based on the total weight of the charged substances in the reactor, followed by 30 minutes of stirring at 80° C. At 110° C. under a normal pressure, 19 kg (50% by weight based on the toluene charged into the reactor) of toluene was removed by evaporation. Subsequently, ethylene oxide was added at 120° C. until n reached 300 to obtain a compound (g) which is a polyethylene oxide derivative.

As a result of analysis by gel permeation chromatography, the retention times of the elution-starting point A and the elution-ending point D were 18.508 minutes and 24.708 minutes, respectively. The retention time of Ptop was 20.067 and the retention times of the points B and C at which the height of the elution curve from PbaseL reached 1/30 of the height of PtopH were 19.642 minutes and 21.217 minutes, respectively. Parea was 838,963 and PareaM, PareaH, and PareaL were 773,189, 9,900, and 55,874, respectively.

From the results, the following are calculated.

$PareaM/Pareax100=92.1(\%)$ $PareaH/Pareax100=1.2(\%)$ $PareaL/Pareax100=6.7(\%)$ When comparison with Example 1 was conducted based on the results shown in Table 1, impurities increased such that low-molecular-weight one was 6.7%. The reason for the increase is that, since the amount of contaminated water as a precursor of the low-molecular-weight impurity, which is concomitant with the toluene addition, is about 3 times larger than that in Example 1, water remains after the removal of toluene by evaporation.

Comparative Example 3

The amounts of toluene to be added and to be removed by evaporation were changed in the operation procedure of Comparative Example 1 as follows. After ethylene oxide was added until n reached 225, 9 kg (28% by weight) of anhydrous toluene was added based on the total weight of the charged substances in the reactor, followed by 30 minutes of stirring at 80° C. At 110° C. under a normal pressure, 3 kg (30% by weight based on the toluene charged into the reactor) of toluene was removed by evaporation. Subsequently, ethylene oxide was added at 120° C. until n reached 300 to obtain a compound (g) which is a polyethylene oxide derivative.

As a result of analysis by gel permeation chromatography, the retention times of the elution-starting point A and the elution-ending point D were 18.758 minutes and 24.433 minutes, respectively. The retention time of Ptop was 20.292 and the retention times of the points B and C at which the height of the elution curve from PbaseL reached 1/30 of the height of PtopH were 19.908 minutes and 20.925 minutes, respectively. Parea was 902,463 and PareaM, PareaH, and PareaL were 851.022, 5,415, and 46,026, respectively.

From the results, the following are calculated.

PareaM/Pareax100=94.3(%)

PareaH/Pareax100=0.6(%)

PareaL/Pareax100=5.1(%)

When comparison with Example 1 was conducted based on the results shown in Table 1, impurities increased such that low-molecular-weight one was 5.1%. The reason for the increase is that, since the amount of toluene added is 10% smaller than that in Example 1, the viscosity in the reactor cannot be sufficiently decreased by dilution and water as a precursor of low-molecular-weight impurity remains after the removal of toluene by evaporation.

Comparative Example 4

Into a reactor for alkylene oxide addition were charged 149 g (about 0.9 mol) of diglycerin and 51 g (34% by weight based on the raw material) of sodium methylate, and methanol removal was carried out at 80° C. under a vacuum condition of 13.3 kPa or lower for 1 hour. Subsequently, after ethylene oxide was added at 120° C. until n reached 170, 12 kg (44% by weight) of anhydrous toluene was added based on the total weight of the charged substances in the reactor, followed by 30 minutes of stirring at 80° C. At 110° C. under a normal pressure, 4 kg (33% by weight based on the toluene charged into the reactor) of toluene was removed by evaporation. Subsequently, ethylene oxide was added at 120° C. until n reached 225 to obtain a compound (d) which is a polyethylene oxide derivative (process yield: 91.5%).

As a result of analysis by gel permeation chromatography, the retention times of the elution-starting point A and the elution-ending point D were 20.083 minutes and 23.933 minutes, respectively. The retention time of Ptop was 20.792 and the retention times of the points B and C at which the height from PbaseL of the elution curve reached 1/30 of the height of PtopH were 20.325 minutes and 21.592 minutes, respectively. Parea was 756,097 and PareaM, PareaH, and PareaL were 716,780, 3,780, and 35,537, respectively.

From the results, the following are calculated.

PareaM/Pareax100=94.8(%)

PareaH/Pareax100=0.5(%)

PareaL/Pareax100=4.7(%)

When comparison with Example 2 was conducted based on the results shown in Table 1, it was shown that the amount of low-molecular-weight impurities was such a large amount as 4.7%. The reason for the increase of the low-molecular-weight impurities is that the methanol removal is insufficient at 80° C. under a vacuum condition of 13.3 kPa or lower owing to the high viscosity. From the results, it is found difficult to produce a highly pure and high-molecular-weight polyoxyalkylene derivative without the step of decreasing the viscosity by addition polymerization of an alkylene oxide (corresponding to the step (C)).

TABLE 1

Analytical Data on Gel Permeation Chromatography

| | Gel permeation chromatography | | | |
|---|---|---|---|---|
| | PareaM/ Parea × 100 | PareaH/ Parea × 100 | PareaL/ Parea × 100 | Total amount of impurities |
| Example 1 | 95.8% | 0.6% | 3.6% | 4.2% |
| Example 2 | 96.9% | 0.4% | 2.7% | 3.1% |
| Comparative Example 1 | 91.2% | 0.9% | 7.9% | 8.8% |
| Comparative Example 2 | 92.1% | 1.2% | 6.7% | 7.9% |
| Comparative Example 3 | 94.3% | 0.6% | 5.1% | 5.7% |
| Comparative Example 4 | 94.8% | 0.5% | 4.7% | 5.2% |

Example 3

Succinic anhydride as a model molecule of a drug was reacted with the hydroxyl group terminal end of the compound (d) obtained in Example 2 and a monofunctional impurity derived from the catalyst, which is a low-molecular-weight impurity, was isolated and quantitatively determined by normal phase liquid chromatography. For the normal phase liquid chromatography, Alliance 2695 Separations Module is used as an HPLC system, Waters 2414 as a differential refractometer, and Shodex Asahipak ES-502N 7C (φ7.5 mm×100 mm) as an HPLC column. The measurement of a sample is carried out by controlling temperature of the column constant-temperature bath at 30° C., letting 5 mM formic acid buffer flow as a developing solvent at a flow rate of 1 ml/minute, and injecting 0.1 ml of a 1% by weight of the sample. Various measured date are obtained by analyzing an elution curve with Waters Empower 2 calculation program.

Into a four-neck flask fitted with a reflux apparatus, a nitrogen gas-introducing tube, a thermometer, and a mixing apparatus was charged 15 g (1.5 mmol) of the compound (d) obtained in Example 2, which was then dissolved in 120 g of toluene. Thereto were added 0.15 g of sodium acetate and 15 mg of dibutylhydroxytoluene (BHT), followed by superheating under reflux to effect azeotropic removal of water. Then, 1.50 g (15.0 mmol) of cinic anhydride was added and reaction was carried out at 110° C. for 5 hours. After completion of the reaction, filtration was carried out and 100 g of hexane was added to the filtrate to precipitate crystals. The crystals were filtrated and, after drying, were analyzed by the normal phase liquid chromatography.

Comparative Example 5

Succinic anhydride as a model molecule of a drug was reacted with the hydroxyl group terminal end of the compound (d) obtained in Comparative Example 4, and a monofunctional impurity derived from the catalyst, which is a low-molecular-weight impurity, was isolated and quantitatively determined by the normal phase liquid chromatography. Into a four-neck flask fitted with a reflux apparatus, a nitrogen gas-introducing tube, a thermometer, and a mixing apparatus was charged 15 g (1.5 mmol) of the compound (d) obtained in Comparative Example 4, which was then dissolved in 120 g of toluene. Thereto were added 0.15 g of sodium acetate and 15 mg of BHT, followed by superheating under reflux to effect azeotropic removal of water. Then, 1.50 g (15.0 mmol) of succinic anhydride was added and reaction was carried out at 110° C. for 5 hours. After completion of the reaction, filtration was carried out and 100 g of hexane was added to the filtrate to precipitate crystals. The crystals were filtrated and, after drying, were analyzed by the normal phase liquid chromatography.

Table 2 shows results of the quantitative determination of the monofunctional impurity. The amount was extremely low as 0.2% in Examples 3 but was large as 2.7% in Comparative Example 5. Thus, it was shown that there was also a significant difference in the modification of the model molecule of a drug.

TABLE 2

Analytical Data on Normal Phase Liquid Chromatography

| | Peak derived from monofunctional impurity (%) |
|---|---|
| Example 3 | 0.2% |
| Comparative Example 5 | 2.7% |

As mentioned above, in the production of the highly pure, high-molecular-weight, and multifunctional polyoxyalkylene derivative of the invention, since methanol derived from the sodium methylate catalyst is removed by the viscosity-decreasing step, it is a characteristic feature that the monofunctional impurity derived from methanol is formed in only an extremely small amount. The monofunctional impurity has a molecular weight ¼ time that of the objective compound and, when such a low-molecular-weight impurity is mixed in, drug circulation in blood decreases. From the results of Table 2, it is shown that the polyoxyalkylene derivative obtained by the producing method of the present application contains the monofunctional impurity in only an extremely small amount and is excellent in homogeneity, so that it is understood that the derivative is a compound with which expected pharmaceuticals and expected gel performance are obtained.

What is claimed is:

1. A method for producing a polyoxyalkylene derivative represented by the following general formula (1):

$$Z\text{-}[(OA)_n\text{-}OH]_m \quad (1)$$

wherein Z is a residue of glycerin or diglycerin, OA is an oxyalkylene group having 2 to 4 carbon atoms, n is an average number of moles of the oxyalkylene group added and is 80 to 800, and m is 3 to 4, the method comprising:

step (A): a step of removing water from glycerin or diglycerin at 90° C. to 170° C. under 3 kPa or lower;

step (B): a step of adding metal sodium or metal potassium as an alkali catalyst in an amount of 0.015 to 1.6% by weight based on the amount of glycerin or diglycerin charged in the step (A) and dissolving the metal at 20 to 110° C.;

step (C): a step of subjecting an alkylene oxide to addition reaction at 50° C. to 110° C. until the average number n of moles of the oxyalkylene group OA added reaches 1 to 10;

step (D): a step of adding an alkali catalyst represented by the following general formula (2) in an amount of 2 to 50% by weight based on glycerin or diglycerin charged in the step (A):

$$R\text{—}OW \quad (2)$$

wherein R is a hydrocarbon group having 1 to 4 hydrocarbons and W represents either sodium or potassium;

step (E): a step of carrying out alcohol removal at 90 to 130° C. under 15 kPa or lower; and step (F): a step of subjecting an alkylene oxide to addition reaction at 100° C. to 130° C. until the average number n of moles of the oxyalkylene group OA added reaches 80 to 800.

2. The method for producing a polyoxyalkylene derivative according to claim 1, wherein the above step (F) is a step of subjecting an alkylene oxide to addition reaction at 100° C. to 130° C. until the average number n of moles of the oxyalkylene group OA added reaches 80 to 300, subsequently adding a hydrocarbon solvent in an amount of 30 to 70% by weight based on total weight in the reaction vessel, then removing 20 to 60% by weight of the hydrocarbon solvent in the reaction vessel by evaporation, and subsequently subjecting an alkylene oxide to addition reaction at 100° C. to 130° C. until the average number n of moles of the oxyalkylene group OA added reaches 300 to 800.

* * * * *